(12) United States Patent
Donderici

(10) Patent No.: US 9,803,466 B2
(45) Date of Patent: Oct. 31, 2017

(54) IMAGING OF WELLBORE PIPES USING DEEP AZIMUTHAL ANTENNAS

(71) Applicant: Halliburton Energy Services, Inc., Houston, TX (US)

(72) Inventor: Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/889,327

(22) PCT Filed: Jul. 2, 2015

(86) PCT No.: PCT/US2015/039032
§ 371 (c)(1),
(2) Date: Nov. 5, 2015

(87) PCT Pub. No.: WO2016/007380
PCT Pub. Date: Jan. 14, 2016

(65) Prior Publication Data
US 2016/0168974 A1 Jun. 16, 2016

Related U.S. Application Data

(60) Provisional application No. 62/023,459, filed on Jul. 11, 2014.

(51) Int. Cl.
*G01N 27/90* (2006.01)
*E21B 47/00* (2012.01)
*G01V 3/28* (2006.01)

(52) U.S. Cl.
CPC ...... *E21B 47/0006* (2013.01); *E21B 47/0002* (2013.01); *G01N 27/90* (2013.01); *G01V 3/28* (2013.01)

(58) Field of Classification Search
CPC .. E21B 47/00; E21B 47/0006; E21B 47/0002; G01N 27/90; G01V 3/28
(Continued)

(56) References Cited

U.S. PATENT DOCUMENTS 2,790,140 A * 4/1957 Bender ............... G01N 27/9033
324/220
3,209,243 A * 9/1965 Walters ................. E21B 47/082
324/220

(Continued)

FOREIGN PATENT DOCUMENTS

WO 2016007380 A1 1/2016

OTHER PUBLICATIONS

Haugland, S.M., Fundamental Analysis of the Remote-Field Eddy-Current Effect, IEEE Transactions on Magnetics, vol. 32, No. 4, 1996.

(Continued)

*Primary Examiner* — Jay Patidar
(74) *Attorney, Agent, or Firm* — McDermott Will & Emery LLP

(57) ABSTRACT

A pipe inspection tool includes a body having a central axis, and one or more azimuthal antenna arrays operatively coupled to the body. Each azimuthal antenna array includes a plurality of antenna coils arranged circumferentially about the central axis and comprising an azimuthal array of z-coils or an azimuthal array of separated x-coils and separated y-coils. The separated x-coils are oriented in a first direction with respect to the central axis, the separated y-coils are oriented in a second direction with respect to the central axis, and the z-coils are oriented in a third direction with respect to the central axis. The second direction is orthogonal to the first direction, and the third direction is orthogonal to both the first and second directions.

20 Claims, 9 Drawing Sheets

(58) Field of Classification Search
USPC ............... 324/220–221, 238; 73/152.57; 166/250.05
See application file for complete search history.

(56) References Cited

U.S. PATENT DOCUMENTS

| | | | | |
|---|---|---|---|---|
| 5,049,817 | A * | 9/1991 | Cecco | G01N 27/904 324/220 |
| 5,955,884 | A * | 9/1999 | Payton | G01V 3/26 324/339 |
| 6,281,678 | B1 * | 8/2001 | Auville | G01N 27/902 324/220 |
| 7,560,920 | B1 | 7/2009 | Ouyang et al. | |
| 8,823,369 | B2 * | 9/2014 | Segletes | G01N 27/84 324/216 |
| 2005/0189945 | A1 | 9/2005 | Reiderman | |
| 2009/0101337 | A1 * | 4/2009 | Neidhardt | E21B 47/08 166/250.01 |
| 2009/0195244 | A1 | 8/2009 | Mouget et al. | |
| 2012/0095686 | A1 | 4/2012 | Legendre et al. | |
| 2012/0306500 | A1 * | 12/2012 | Bittar | E21B 47/024 324/338 |
| 2013/0105224 | A1 * | 5/2013 | Donderici | G01V 3/30 175/45 |
| 2013/0193953 | A1 * | 8/2013 | Yarbro | E21B 47/082 324/76.77 |

OTHER PUBLICATIONS

Al-Yateem, et al., Measuring and Profiling Casing Corrosion for Predicting Subsurface Leaks, IPTC 17170, 2013.
Brill, et al., Electromagnetic Casing Inspection Tool for Corrosion Evaluation, IPTC 14865, 2012.
Arbuzov et al., Memory Magnetic Imaging Defectoscopy, SPE 162054, 2012.
Garcia, et al., Successful Application of a New Electromagnetic Corrosion Tool for Well Integrity Evaluation in Old Wells Completed with Reduced Diameter Tubular, IPTC 16997, 2013.
International Search Report and Written Opinion for PCT/US2015/039032 dated Sep. 24, 2015.
Magnetic Thickness Tool, Company: GE Energy—GE, Tool: Sondex Wireline Tools—Cased Hole Products, 2003.

* cited by examiner

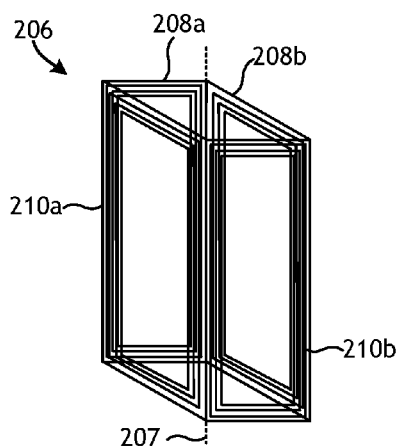 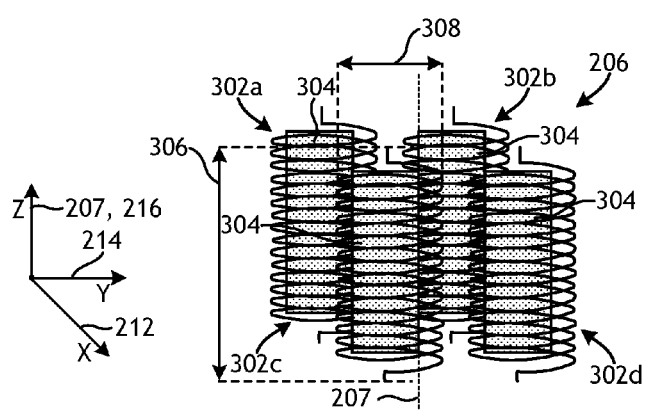
FIG. 3A   FIG. 3B
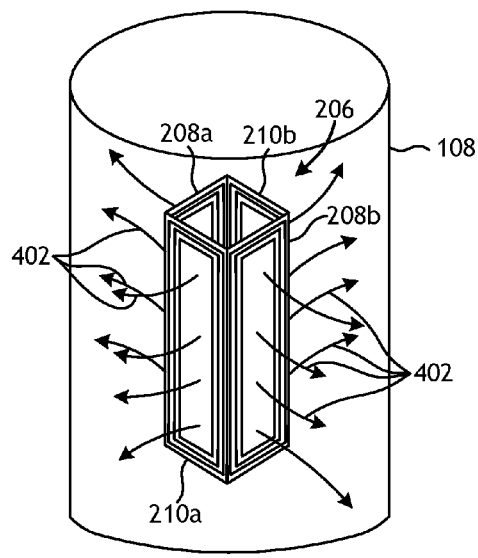 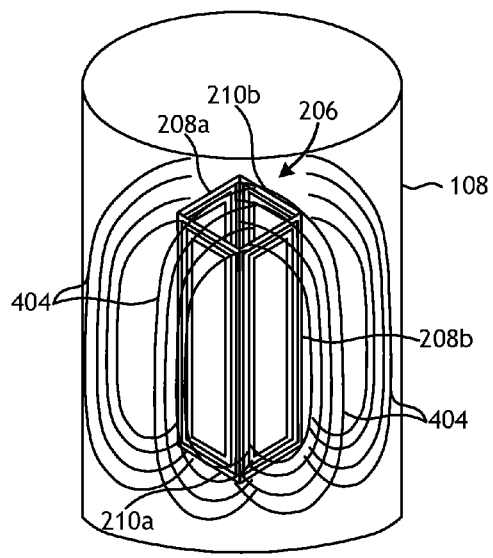
FIG. 4A   FIG. 4B

IMAGING OF WELLBORE PIPES USING DEEP AZIMUTHAL ANTENNAS

CROSS-REFERENCE TO RELATED APPLICATIONS

The present application claims priority to U.S. Provisional Patent App. Ser. No. 62/023,459, filed on Jul. 11, 2014.

BACKGROUND

Wellbores in the oil and gas industry are typically drilled using a drill string with a drill bit secured to its distal end. The drilled wellbore is subsequently completed by cementing a string of metal pipes connected end-to-end within the wellbore. Commonly called "casing," such strings of metal pipes increase the structural stability of the wellbore and provide a flow path between the earth's surface and selected subterranean formations. Moreover, in some wellbores, one or more production pipes are extended into the wellbore to provide a conduit for hydrocarbons to be conveyed to the earth's surface. Accordingly, as used herein, the term "pipe" or "wellbore pipe" will refer to metal pipes or pipelines that line the walls of a wellbore, such as casing, and also production pipes extended into a wellbore to facilitate hydrocarbon production operations.

During the lifetime of a well, wellbore pipes are exposed to high volumes of materials and fluids required to pass through them, including chemically aggressive fluids. In harsh environments, however, the pipes may be subject to corrosion that may affect their functionality. Timely and accurate detection of structural integrity problems such as cracks, pinholes, and corrosion is essential to reducing costs associated with wellbore intervention, since pulling wellbore pipes, such as casing, out of a wellbore for further inspection and repairs and replacing can be a very expensive task.

Some wellbores include multiple concentric pipes or strings of casing secured within the wellbore with an innermost pipe that exhibits a relatively narrow diameter. As will be appreciated, the diameter of the innermost pipe limits the size of the monitoring and intervention system that can be deployed to monitor the integrity of all of the concentric pipes. With multiple concentric pipes, another problem is the ability to effectively monitor the outermost pipes from the innermost pipe, since any monitoring system has to be able to sense through a number of pipe layers, each of which may have developed distinct problems or defects.

Several different sensing methods have been proposed for detecting corrosion and other types of defects in pipelines, some of which have been applied to wellbore pipes used for extracting hydrocarbons. The most common method utilizes acoustic wave pulses and analysis of reflections from the surface of a pipe wall to image any defects. Electromagnetic inspection methods are also used for the same purpose, and are desirable since they allow an operator to sense beyond the first pipe, and thereby obtain measurements from second, third, or additional pipes beyond the third pipe. Existing pipe inspection methods, however, are either azimuthally sensitive and shallow or azimuthally insensitive and deep.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 3A and 3B depict alternative embodiments for the azimuthal antenna arrays of FIG. 2.

FIGS. 4A and 4B illustrate schematic views of exemplary azimuthal antenna arrays within a wellbore pipe.

DETAILED DESCRIPTION

The present disclosure is related to wellbore monitoring and, more particularly, to azimuthal antenna arrays that provide azimuthal sensing beyond a first wellbore pipe.

Embodiments of the present disclosure provide new and improved electromagnetic inspection methods for wellbore pipes, such as strings of casing or production pipes extended into a wellbore. The presently described methods rely on azimuthal arrays of elongated z-coil or separated x- and y-coil antennas. As compared to conventional coil antennas and conventional electromagnetic inspection methods, the coil antennas of the present disclosure and related methods can provide azimuthal sensing of wellbore pipes that lie radially beyond the first or innermost wellbore pipe, that is, the ability to sense second, third, and further wellbore pipes concentrically arranged about the first wellbore pipe. More particularly, conventional coil antennas are able to sense beyond the first pipe using only z-coils, which are not azimuthally sensitive. In contrast, the proposed method uses azimuthal arrays of elongated z-coils or separated x- and y-coils (on sensor pads or positioned in the pipe inspection tool itself) that can simultaneously see deep and provide high resolution deep images about features of wellbore pipes beyond the first pipe. As a result, the embodiments described herein help facilitate measurement of azimuthal distribution of defects on wellbore pipes as opposed to the volumetric approach of conventional coil antennas.

Figure 1:
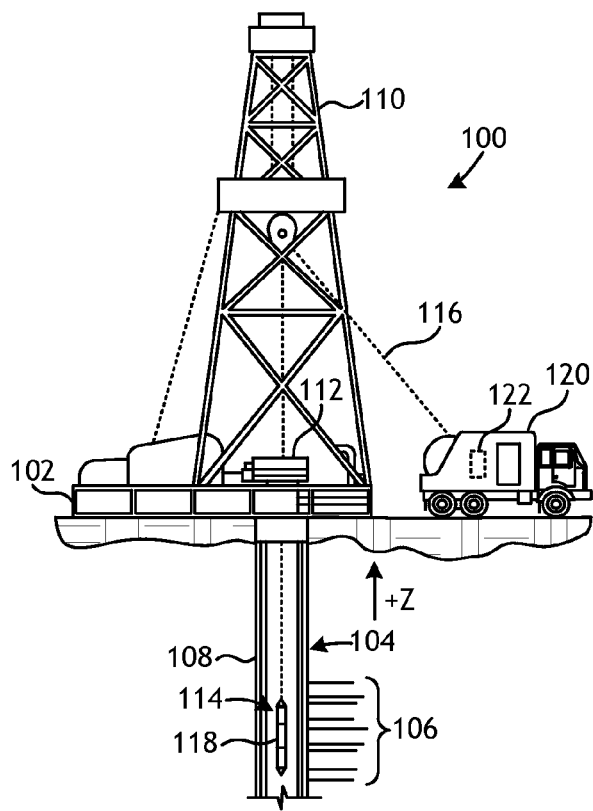
FIG. 1 is a schematic diagram of an exemplary wireline system that may employ the principles of the present disclosure.

FIG. 1 is a schematic diagram of an exemplary wireline system 100 that may employ the principles of the present disclosure, according to one or more embodiments. As illustrated, the wireline system 100 may include a surface platform 102 positioned at the earth's surface and a wellbore 104 that extends from the surface platform 102 into one or more subterranean formations 106. In other embodiments, such as in offshore operations, a volume of water may separate the surface platform 102 and the wellbore 104. The wellbore 104 may be lined with one or more pipes 108, also referred to as strings of casing. In some embodiments, portions of the wellbore 104 may have only one pipe 108 positioned therein, but other portions of the wellbore 104 may be lined with two or more concentrically disposed pipes 108. The pipes 108 may be made of plain carbon steel, stainless steel, or another material capable of withstanding a variety of forces, such as collapse, burst, and tensile failure.

The wireline system 100 may include a derrick 110 supported by the surface platform 102 and a wellhead installation 112 positioned at the top of the wellbore 104. A pipe inspection tool 114 may be suspended into the wellbore 104 on a cable 116. In some embodiments, the pipe inspection tool 114 may alternatively be suspended within a production pipe (not shown) positioned within the pipes 108 that line the wellbore 104 (i.e., casing). In such embodiments, the production pipe may extend by itself within the pipes 108 or alternatively be positioned adjacent one or more eccentrically located production pipes that are also positioned within the pipes 108. Accordingly, as used herein, "pipes 108" may refer to strings of casing that line the wellbore 104 and/or at least one production pipe extended into the wellbore 104.

The pipe inspection tool 114 may comprise an electromagnetic, non-destructive inspection tool. Its operation may be based on either the flux-leakage principle or the eddy-current principle, or a combination thereof, and may be insensitive to non-magnetic deposits and is operable irrespective of the nature of the fluid mixture flowing into/out of the wellbore 104. The pipe inspection tool 114 can be used for the detection of localized damage or defects in the pipes 108. In operation, the pipes 108 are subjected to a strong primary magnetic field produced by the pipe inspection tool 114 and, due to their ferromagnetic nature, eddy currents will be generated inside the pipes. These eddy currents produce secondary magnetic fields that are measured along with the primary magnetic field with the tool 114. In the presence of discontinuities or defects in the metal of the pipes 108, such as pits and holes caused by corrosion, the changes in the secondary magnetic field can be detected with the pipe inspection tool 114.

To accomplish this, the pipe inspection tool 114 may include one or more electromagnetic sensors 118, which may be communicably coupled to the cable 116. The cable 116 may include conductors for conveying power to the pipe inspection tool 114 and also for facilitating communication between the surface platform 102 and the pipe inspection tool 114. A logging facility 120, shown in FIG. 1 as a truck, may collect measurements from the electromagnetic sensors 118, and may include computing facilities 122 for controlling, processing, storing, and/or visualizing the measurements gathered by the electromagnetic sensors 118. The computing facilities 122 may be communicably coupled to the pipe inspection tool 114 by way of the cable 116.

The electromagnetic sensors 118 may include one or more electromagnetic coil antennas that may be used as transmitters, receivers, or a combination of both (i.e., transceivers) for obtaining in situ measurements of the pipe(s) 108 and thereby determining the structural integrity or condition of each pipe 108. Multiple measurements may be made by the electromagnetic sensors 118 as the pipe inspection tool 114 is lowered into the wellbore 104 (i.e., "down log") and/or raised back to the surface of the well (i.e., "up log"). Each measurement gives an indication of the condition of the pipes 108 at the specific depth where the pipe inspection tool 114 is located.

The principle of measurement is based on two separate mechanisms: magnetic fields that follow the magnetically shortest path (such as in magnetic circuits) and eddy currents that are induced on the pipes 108, which create signals as a function of the electromagnetic skin depth of the pipes 108. Received signals are also affected by casing collars and natural changes in the magnetic properties of different pieces of a wellbore pipe. After received signals are recorded, they are interpreted by an algorithm, and features of the pipes 108 can be calculated from the measurements. These calculations and determinations can be undertaken, for example, using the computing facilities 122 at the logging facility 120. Advantageously, electromagnetic inspection tools, such as the pipe inspection tool 114, provide a capability to make measurements of the pipes 108 beyond the first or innermost wellbore pipe.

In some embodiments, the electromagnetic sensors 118 may be designed to operate in a centralized position within the innermost pipe 108, such as through the use of one or more centralizers (not shown) attached to the body of the pipe inspection tool 114. In other embodiments, however, the electromagnetic sensors 118 may be designed to be adjacent or in intimate contact with the inner wall of the innermost pipe 108. In such embodiments, the electromagnetic sensors 118 may be mounted on one or more deployable sensor pads (not shown) positioned on actuatable arms (not shown) that move the electromagnetic sensors 118 radially outward toward the inner wall of the innermost pipe 108.

Figure 2:
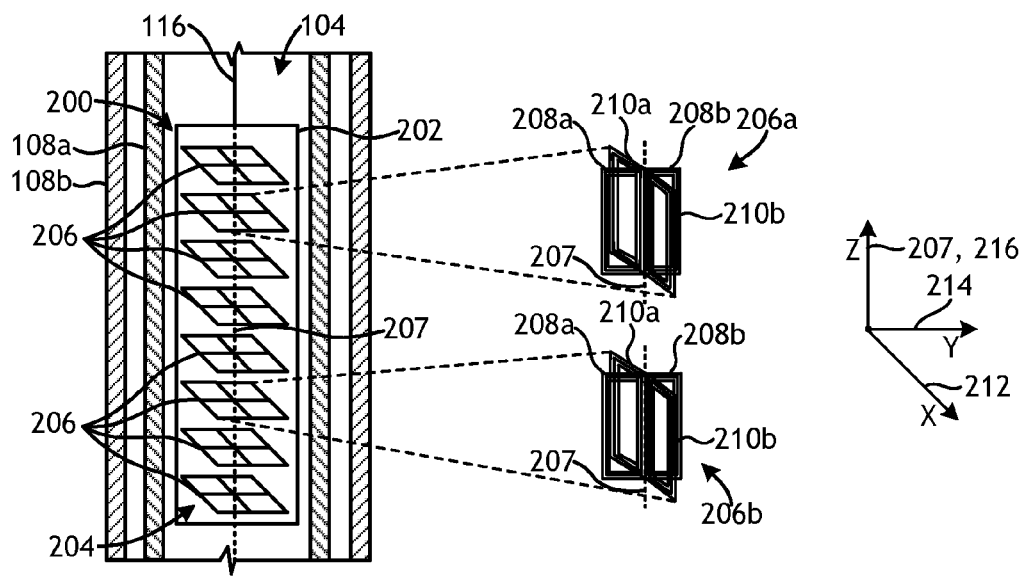
FIG. 2 is a schematic side view of an exemplary pipe inspection tool.

FIG. 2 is a schematic side view of an exemplary pipe inspection tool 200, according to one or more embodiments. The pipe inspection tool 200 may be similar to or the same as the pipe inspection tool 114 of FIG. 1 and, therefore, may be used to monitor the pipes 108 positioned within the wellbore 104. In the illustrated embodiment, the pipes 108 are shown as a first pipe 108a and a second pipe 108b, where the first pipe 108a is the innermost wellbore pipe and is located within the second pipe 108b. In some embodiments, the first and second pipes 108a,b may line the walls of the wellbore 104 as concentric strings of casing or liner. In other embodiments, however, the first pipe 108a may comprise a production pipe concentrically- or eccentrically-positioned within the second pipe 108b, which may comprise casing that lines the wellbore 104, without departing from the scope of the disclosure. As will be appreciated, more than two wellbore pipes 108a,b may be used in any of the embodiments described herein.

As illustrated, the pipe inspection tool 200 is lowered into the wellbore on the cable 116 and includes a body 202 and at least one electromagnetic sensor 204 positioned within or otherwise operatively coupled to the body 202. The electromagnetic sensor 204 may be similar to or the same as the electromagnetic sensor 118 of FIG. 1 and may include a plurality of azimuthal antenna arrays 206. In the illustrated embodiment, the azimuthal antenna arrays 206 are depicted as being axially spaced from each other along the length of the body 202. In other embodiments, however, one or more of the azimuthal antenna arrays 206 may be mounted on deployable sensor pads (not shown) and extendable toward the inner wall of the first pipe 108a, as discussed in more detail below.

Each azimuthal antenna array 206 may include three or more antenna coils arranged azimuthally (i.e., circumferentially) with respect to each other and otherwise about a central axis 207 of the body 202. It is noted here that the principles of the disclosure can also work with two antenna coils that are azimuthally separated, but performance of such a configuration may deteriorate significantly depending on the azimuth angle of the defect, and a unique solution may not be possible to obtain due to limited information. In the illustrated embodiment, eight azimuthal antenna arrays 206 are depicted, where each azimuthal antenna array 206 includes four antenna coils arranged about the central axis 207. Accordingly, the electromagnetic sensor 204 may include thirty-two antenna coils. It will be appreciated, however, that more or less than eight azimuthal antenna arrays 206 may be employed, and the azimuthal antenna arrays 206 may include more or less than four antenna coils (at least three), without departing from the scope of the disclosure.

The antenna coils in each azimuthal antenna array 206 may comprise an azimuthal array of z-coils or separated x-coils and y-coils, where each antenna coil of the azimuthal antenna array 206 is in the same plane that is substantially perpendicular to the axial direction (i.e., the central axis 207). In at least one embodiment, however, the antenna coils in any of the azimuthal antenna array 206 may comprise a combination of any z-coils and separated x-coils and y-coils. As compared to conventional antenna coils used in pipe inspection tools, the azimuthal antenna arrays 206 of the present disclosure can provide azimuthal sensing of the wellbore pipes beyond the first pipe 108a, that is, the second pipe 108b and any wellbore pipes spaced radially outward from the second pipe 108b. Moreover, the presently described azimuthal antenna arrays 206 allow measurement of azimuthal distribution of defects (i.e., corrosion) in the pipes 108a,b, as opposed to the volumetric approach of prior art systems. As a result, embodiments of the present disclosure can provide higher resolution azimuthal images of any wellbore pipes radially beyond the first pipe 108a.

Two enlarged azimuthal antenna arrays 206 are depicted in FIG. 2 as a first azimuthal antenna array 206a and a second azimuthal antenna array 206b. In the illustrated embodiment, each azimuthal antenna array 206a,b may include two separated x-coils 208a and 208b and two separated y-coils 210a and 210b, where the x- and y-coils 208a,b and 210a,b are circumferentially spaced about the central axis 207. As discussed below, the x-coils 208a,b and the y-coils 210a,b may alternatively be replaced with three or more z-coils, without departing from the scope of the disclosure.

While not expressly shown in the enlarged views of FIG. 2, the azimuthal antenna arrays 206a,b may each include a bobbin or core about which the x- and y-coils 208a,b, 210a,b are wound. More particularly, the core may have a central hole that extends between axial ends of the core, and the windings of the x- and y-coils 208a,b, 210a,b may be wound about the periphery of the core and through the central hole in their respective azimuthal directions. The core may be made of a magnetically permeable material and may help amplify or boost electromagnetic signals emitted by the azimuthal antenna arrays 206a,b.

The x-coils 208a,b may be oriented in a first direction 212, and the y-coils 210a,b may be oriented in a second direction 214, where the second direction 214 is orthogonal to the first direction 212. The first direction 212 may constitute the x-direction with respect to the central axis 207 and the second direction 214 may constitute the y-direction with respect to the central axis 207, which is 90° offset from the first direction 212. Accordingly, in the illustrated embodiment, the x-coils 208a,b are aligned along a common plane that extends in the x-direction (i.e., the first direction 212), and the y-coils 210a,b are aligned along a common plane that extends in the y-direction (i.e., the second direction 214). The central axis 207 extends in a third direction 216 orthogonal to both the first and second directions 212, 214 and otherwise parallel to the longitudinal axis of the wellbore 104. Accordingly, the third direction 216 may constitute the z-direction with respect to the central axis 207 and may be 90° offset from both the first and second directions 212, 214.

Upon exciting the x- and y-coils 208a,b, 210a,b of one or both of the azimuthal antenna arrays 206a,b, such as through the influx of an alternating current or a voltage, magnetic fields (not shown) may be generated that extend radially away from the pipe inspection tool 200 and penetrate at least one of the pipes 108a,b. Because of their mutually orthogonal orientation, the magnetic fields generated by the x- and y-coils 208a,b and 210a,b may also be mutually orthogonal to each other. In some embodiments, the first azimuthal antenna array 206a may operate as a transmitting antenna that generates the magnetic fields from an excitation signal, and the second azimuthal antenna array 206b may operate as a receiver antenna that receives and measures response signals derived from the magnetic fields. In other embodiments, however, each azimuthal antenna array 206a,b may operate as a combined transmitter and receiver antenna (i.e., a transceiver), as discussed in more detail below.

FIGS. 3A and 3B depict alternative embodiments for the azimuthal antenna arrays 206 of FIG. 2. The azimuthal antenna arrays 206 of either FIG. 3A or 3B may replace either of the enlarged azimuthal antenna arrays 206a,b of FIG. 2. Similar to the azimuthal antenna arrays 206a,b of FIG. 2, the azimuthal antenna array 206 depicted in FIG. 3A includes two separated x-coils 208a and 208b and two separated y-coils 210a and 210b, where the x- and y-coils 208a,b and 210a,b are circumferentially arranged about the central axis 207. The x-coils 208a,b may be oriented in the first direction 212, and the y-coils 210a,b may be oriented in the second direction 214 such that magnetic fields generated by the x-coils 208a,b may be substantially orthogonal to magnetic fields generated by the y-coils 210a,b. Unlike the azimuthal antenna arrays 206a,b of FIG. 2, however, the x-coils 208a,b in FIG. 3A are aligned along parallel planes that extend in the x-direction (i.e., the first direction 212), and the y-coils 210a,b are aligned along parallel planes that extend in the y-direction (i.e., the second direction 214).

In FIG. 3B, the azimuthal antenna array 206 includes four z-coils 302 (shown as first, second, third, and fourth z-coils 302a, 302b, 302c, and 302d) each wrapped about a corresponding core 304 and each circumferentially arranged about the central axis 207. Each z-coil 302a-d may comprise a continuous solenoid or helical winding pattern that extends longitudinally between the axial upper and lower ends of the corresponding core 304. Some or all of the z-coils 302a-d may be characterized and otherwise referred to herein as "elongated" z-coils. An elongated z-coil may refer to a z-coil that has an axial length 306 that is at least twice as long as the width or diameter 308 of the z-coil.

The windings of the z-coils 302a-d may be wrapped about the corresponding cores 304 in the third direction 216, which, as mentioned above, is orthogonal to both the first and second directions 212, 214 and otherwise parallel to the central axis 207. While depicted in FIG. 3B as exhibiting a generally circular-shape, one or more of the z-coils 302a-d may alternatively exhibit a polygonal profile (e.g., square, rectangular, etc.), without departing from the scope of the disclosure. Upon exciting the z-coils 302a-d, such as through the influx of an alternating current or a voltage, the azimuthal antenna array 206 of FIG. 3B may generate magnetic fields (not shown) that extend axially away from the pipe inspection tool 200 (FIG. 2) in substantially the third direction 216 to penetrate at least one of the pipes 108a,b.

FIGS. 4A and 4B illustrate schematic views of exemplary azimuthal antenna arrays 206 within a wellbore pipe 108. More particularly, the azimuthal antenna arrays 206 shown in FIGS. 4A and 4B may be substantially similar to or the same as the azimuthal antenna array 206 of FIG. 3A. Accordingly, the x-coils 208a,b are aligned along parallel planes that extend in the x-direction (i.e., the first direction 212), and the y-coils 210a,b are aligned along parallel planes that extend in the y-direction (i.e., the second direction 214).

As shown in FIGS. 4A and 4B, there are two different physical mechanisms of sensing. FIG. 4A shows sensing using magnetic fields 402, and FIG. 4B shows sensing using electric fields 404. In the case of magnetic fields 402, the magnetic fields 402 that are generated by a given antenna coil (i.e., one of the x- and y-coils 208a,b, 210a,b) leave one side of the antenna coil, they are split, and then circulate around the pipe(s) 108 azimuthally. The magnetic fields 402 subsequently return to the other side of the antenna coil, thereby closing the magnetic circuit. Due to the azimuthal nature of the magnetic fields 402 on the pipe(s) 108, this type of method is sensitive to vertically oriented defects, since such defects impede the flow of the magnetic fields 402 back to the antenna coil. This type of detection mostly utilizes the fact that the pipe 108 has a magnetic permeability that is different from that of air, which is true for most tubular and casing materials commonly used in the oil and gas industry. It should be noted, however, that this approach may be less effective with chrome pipes.

In the case of electric fields 404, as shown in FIG. 4B, the electric fields 404 that are induced by the alternating magnetic fields 402 travel axially on the pipe 108 and they close a circuit around the given antenna coil. Due to the axial nature of the flow of the electric fields 404 on the pipe(s) 108, this type of method is more sensitive to horizontal defects (i.e., cracks), since such defects impede the flow of electric fields 404 back to themselves. Moreover, this approach is sensitive to both conductivity and magnetic permeability of the pipe(s) 108 since the resistance of the pipe 108 is a function of both. In particular, conductivity directly determines the resistance of the pipe(s) 108 while magnetic permeability is only affected through changes in the skin depth of the pipe(s) 108. When skin depth on the pipe(s) 108 is small, effective electrical thickness of the pipe(s) 108 decreases and resistance per length of the pipe(s) 108 increases. When the skin depth on the pipe(s) 108 is large, however, the effective electrical thickness of the pipe(s) 108 increases and the resistance per length of the pipe(s) 108 decreases.

In operation of the pipe inspection tool 200 of FIG. 2, and any of the pipe inspection tools described herein, both electrical and magnetic sensing mechanisms may be in place simultaneously and the received response signals may be affected by both. Due to complicated physics, numerical interpretation models, as described in more detail below, are usually preferred to analyze the received response signals as opposed to those based on analytical formulas.

Figure 5A:
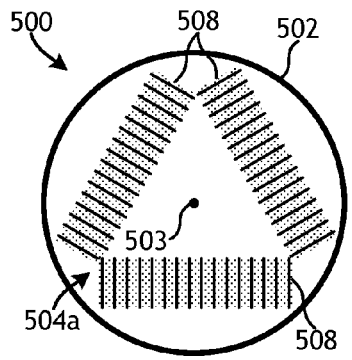
FIGS. 5A-5F depict axial end views of different configurations and embodiments of a pipe inspection tool.
Figure 5B:
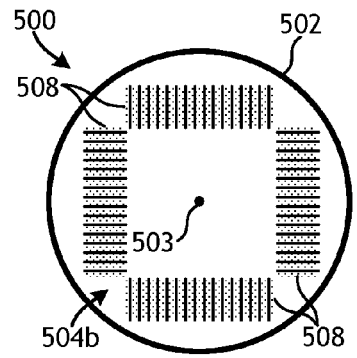
Figure 5C:
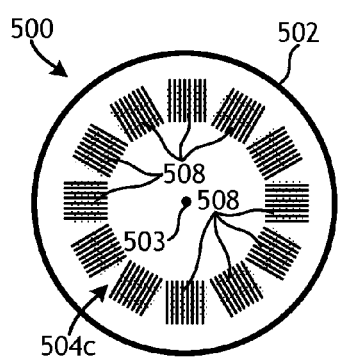
Figure 5D:
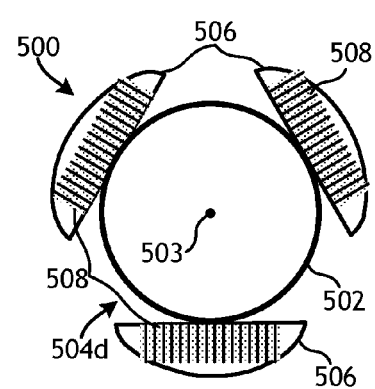
Figure 5E:
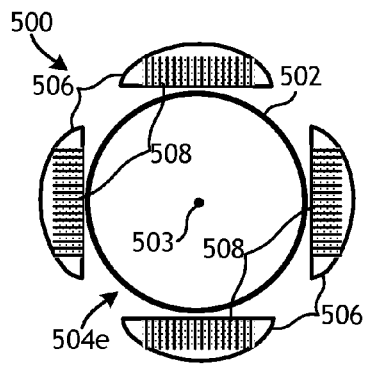
Figure 5F:
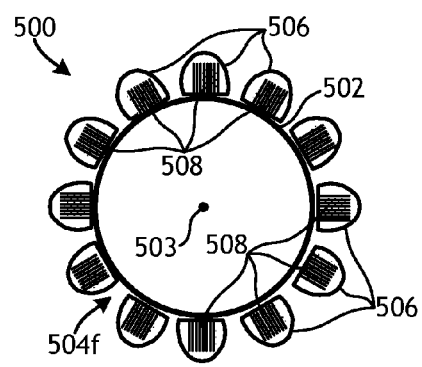

FIGS. 5A-5F show axial end views of different configurations and embodiments of a pipe inspection tool 500, in accordance with the present disclosure. The pipe inspection tool 500 may be the same as or similar to the pipe inspection tool 200 of FIG. 2. For instance, the pipe inspection tool 500 may include a body 502 that has a central axis 503 (shown coming out of the page) and at least one azimuthal antenna array 504 operatively coupled to the body 502 about the central axis 503. More particularly, FIGS. 5A-5C depict azimuthal antenna arrays 504a-504c, respectively, that are mounted to the body 502 about the central axis 503, and FIGS. 5D-5F depict azimuthal antenna arrays 504d-504f that are mounted on deployable sensor pads 506 about the central axis 503. The deployable sensor pads 506 may be configured to move the azimuthal antenna arrays 504d-504f radially outward from the body 502 and toward the inner wall of an innermost pipe (i.e., the first pipe 108a of FIG. 2).

The azimuthal antenna arrays 504a-f each depict at least three antenna coils 508 wrapped about corresponding cores (not labeled). More particularly, each antenna coil 508 is shown as either an x-coil (i.e., the x-coils 208a,b of FIGS. 2 and 3A) or a y-coil (i.e., the y-coils 210a,b of FIGS. 2 and 3A). No z-coils are shown in the azimuthal antenna arrays 504a-f of FIGS. 5A-5F, but it will be appreciated that z-coils could alternatively be used in any of the embodiments.

The three antenna coils 508 of the azimuthal antenna arrays 504a and 504d of FIGS. 5A and 5D, respectively, are depicted as being angularly offset from each other by 120°. As a result, the three antenna coils 508 may constitute antenna coils 508 that are a combination of x- and y-coils, as described herein, and may be able to provide a well operator with measurements of 120° azimuth resolution.

The azimuthal antenna arrays 504b and 504e of FIGS. 5B and 5E, respectively, may be substantially similar to the azimuthal antenna array 206 of FIG. 3A. Accordingly, the x-coils 508 are aligned along parallel planes that extend in the x-direction (i.e., the first direction 212 of FIGS. 2 and 3A-3B), and the y-coils 508 are aligned along parallel planes that extend in the y-direction (i.e., the second direction 214 of FIGS. 2 and 3A-3B), thereby providing a well operator with measurements of 90° azimuth resolution.

The azimuthal antenna arrays 504c and 504f of FIGS. 5C and 5F, respectively, include twelve antenna coils 508 angularly offset from each other by 30°. As a result, the twelve antenna coils 508 may constitute antenna coils 508 that are a combination of x- and y-coils, as described herein, but may be able to provide a well operator with measurements of 30° azimuth resolution.

As will be appreciated, the deployable sensor pads 506 of FIGS. 5C and 5F may help push the antenna coils 508 as far out as possible from the central axis 503, which may result in an increase in azimuthal sensitivity. Due to limited space within the wellbore pipes, however, there is a trade-off between the size and number of antenna coils 508. For example, the twelve antenna coil 508 configuration of FIGS. 5C and 5F may achieve measurements with 30° resolution azimuthally, but the size of the antenna coils 508 will necessarily be smaller, which may result in less signal and lower signal-to-noise ratio.

Figure 6:
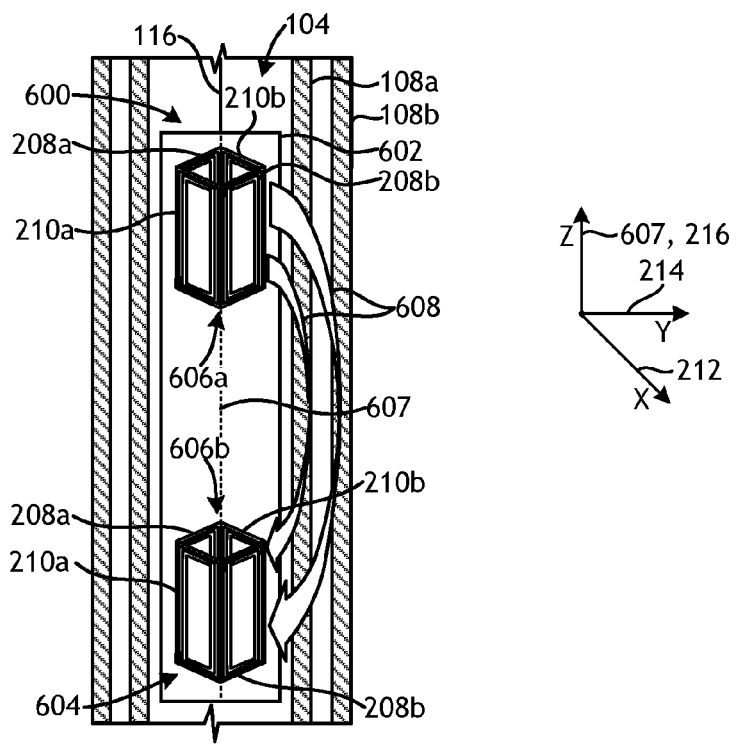
FIG. 6 is a schematic side view of another exemplary pipe inspection tool.

FIG. 6 is a schematic, partial cross-sectional side view of another exemplary pipe inspection tool 600, according to one or more embodiments. The pipe inspection tool 600 may be similar in some respects to the pipe inspection tool 200 of FIG. 2 and, therefore, may be conveyed into the wellbore 104 on the cable 116 and used to monitor the pipes 108a,b positioned within the wellbore 104. The pipe inspection tool 600 includes a body 602 and at least one electromagnetic sensor 604 operatively coupled to the body 602. Similar to the electromagnetic sensor 204 of FIG. 2, the electromagnetic sensor 604 may include a plurality of azimuthal antenna arrays 606 operatively coupled to the body 602 about a central axis 607, and shown in FIG. 6 as a first azimuthal antenna array 606a and a second azimuthal antenna array 606b axially spaced from the first azimuthal antenna array 606a.

The first and second azimuthal antenna arrays 606a,b may be similar to or the same as the azimuthal antenna array 206 of FIG. 3A. Accordingly, each azimuthal antenna array 606a,b may include the two separated x-coils 208a,b and the two separated y-coils 210a,b, where the x-coils 208a,b are aligned along parallel planes that extend in the first direction 212 (i.e., the x-direction), and the y-coils 210a,b are aligned along parallel planes that extend in the second direction 214 (i.e., the y-direction). In other embodiments, however, the first and second azimuthal antenna arrays 606a,b may be similar to any of the other azimuthal antenna arrays described herein, without departing from the scope of the disclosure.

In the illustrated embodiment, the first azimuthal antenna array 606a may operate as a transmitter antenna and the second azimuthal antenna array 606b may operate as a receiver antenna. Upon exciting the x- and y-coils 208a,b, 210a,b of the first azimuthal antenna array 606a, such as through the influx of an alternating current or a voltage, the first azimuthal antenna array 606a may generate magnetic fields 608 that extend radially away from the pipe inspection tool 600 and penetrate at least one of the pipes 108a,b. The magnetic fields 608 may be subsequently received by the second azimuthal antenna array 606b acting as the receiver antenna.

The depth of investigation in eddy current methods is dependent on several factors, the most important being the distance (axial separation) between the transmitter and receiver antennas (i.e., the first and second azimuthal antenna arrays 606a,b). The longer the distance between the transmitter and receiver antennas, the more electric or magnetic fields 608 can travel away from the pipe inspection tool 600 before they complete the circuit. Since magnetic fields 608 and currents always take the shortest path (magnetically and electrically), depth of investigation is also dependent upon the properties of the pipes 108a,b that are involved. For example, if the first or innermost pipe 108a is highly magnetically permeable, most of the magnetic fields 608 will flow on the innermost pipe 108a, and less will flow to any wellbore pipes radially offset from the innermost pipe 108a. In the case where there is increased axial separation between the transmitter and receiver antennas, more flow of the magnetic fields 608 may be achieved in the second pipe 108b or any wellbore pipes radially beyond the first pipe 108a.

In time-domain systems, where a measurement is made as a function of time, received signals at the receiver antenna (i.e., the second azimuthal antenna array 606b) at early times are only sensitive to wellbore pipes that are shallow (i.e., radially close to the pipe inspection tool 600), where received signals that are "late time" are sensitive to both shallow and deep pipes (i.e., radially close and far from the pipe inspection tool 600). In frequency-domain systems, where steady state discrete frequency measurements are made, high frequencies (typically 10-1000 Hz or 1-100 ms) are sensitive to shallow pipe features, while low frequencies (typically 0.1-10 Hz or 100-10000 ms) are sensitive to deep pipe features. The optimum frequency range to sense a particular wellbore pipe depends on the effective distance between the transmitter and receiver antennas and the properties of the pipes that come before the target pipe as electromagnetic waves penetrate them. For example, more conductive and magnetically permeable pipes require lower frequencies (or equivalently later times for time-domain systems), while less conductive and less magnetically permeable pipes require higher frequencies (or equivalently earlier times for time-domain systems).

Figure 7A:
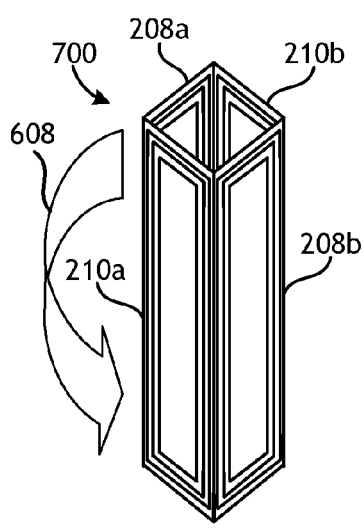
FIGS. 7A and 7B depict schematic diagrams of a transceiver antenna and separate transmitter and receiver antennas, respectively.
Figure 7B:
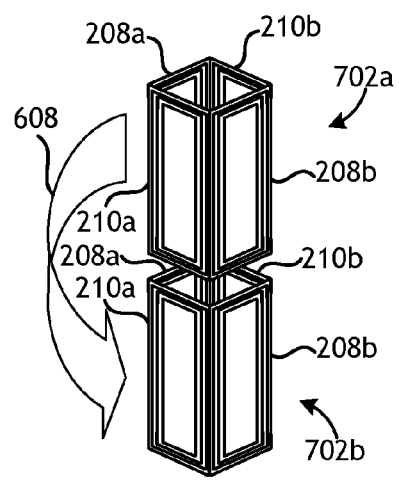

FIGS. 7A and 7B depict schematic diagrams of a transceiver antenna 700 and separate transmitter and receiver antennas 702a,b, respectively. The transceiver antenna 700 of FIG. 7A may be similar in some respects to the azimuthal antenna arrays 206 and 606a,b of FIGS. 3A and 6, respectively, and may therefore include the two separated x-coils 208a,b and the two separated y-coils 210a,b. Alternatively, the transceiver antenna 700 may be similar to any of the other azimuthal antenna arrays described herein, without departing from the scope of the disclosure. Unlike the azimuthal antenna array 606a,b of FIG. 6, however, the transceiver antenna 700 may be used as both a transmitter antenna and a receiver antenna, where the magnetic fields 608 are generated and received by the same antenna structure.

The transmitter and receiver antennas 702a,b of FIG. 7B may be similar to the first and second azimuthal antenna arrays 606a,b of FIG. 6 and may, therefore, also each include the two separated x-coils 208a,b and the two separated y-coils 210a,b. In other embodiments, however, the transmitter and receiver antennas 702a,b may be similar to any of the other azimuthal antenna arrays described herein, without departing from the scope of the disclosure. In operation, the transmitter antenna 702a may generate the magnetic fields 208 that may be subsequently sensed by the receiver antenna 702b.

In cases where the transmitter and receiver antennas are collocated, or where only a single antenna exists for both transmitting and receiving, as in the case of the transceiver antenna 700, the depth of investigation is proportional to the average distance between any combination of windings of transmitter and receiver that could be considered, which is effectively proportional to the length of the transceiver antenna 700.

Figure 8A:
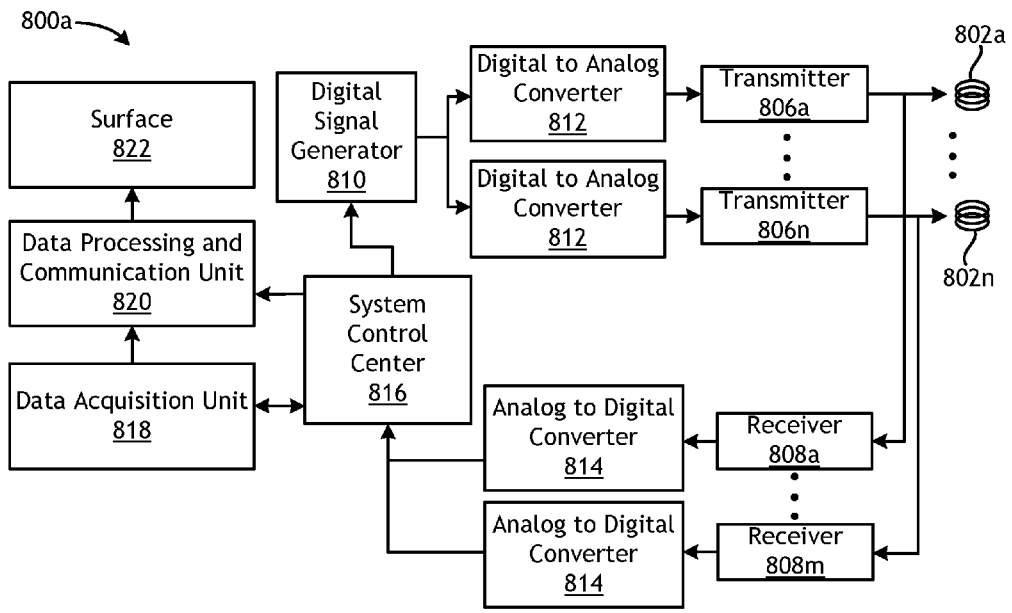
FIGS. 8A and 8B are block diagrams of exemplary data acquisition and control systems that may be used for monitoring pipes in a wellbore.
Figure 8B:
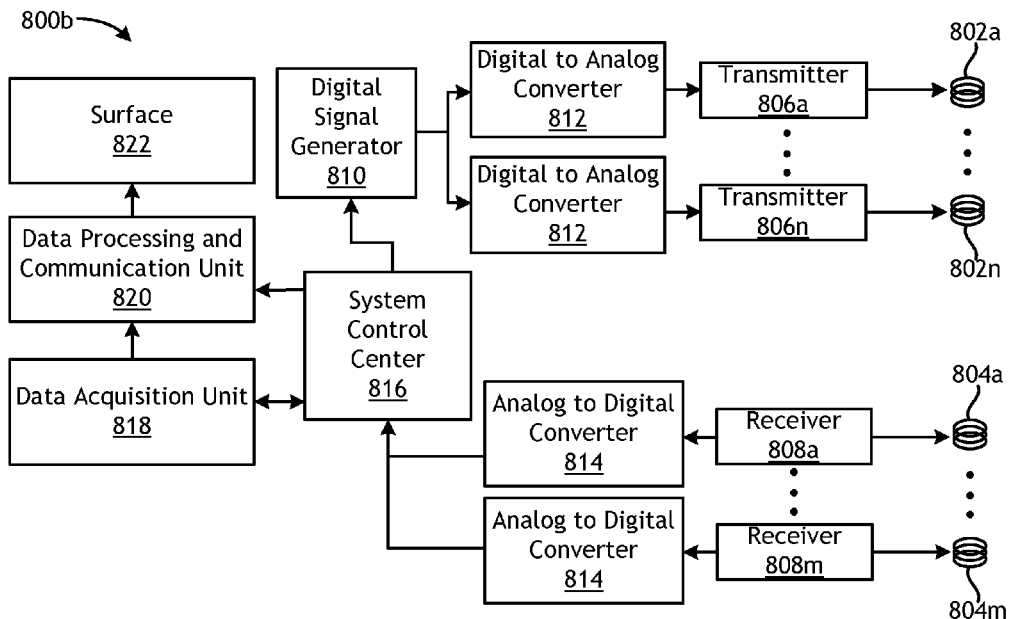

FIGS. 8A and 8B are block diagrams of exemplary data acquisition and control systems 800a and 800b, respectively, which may be used for monitoring pipes in a wellbore, according to one or more embodiments of the present disclosure. More particularly, the data acquisition and control system 800a of FIG. 8A may be used with transceiver antennas, such as the transceiver antenna 700 of FIG. 7A, and the data acquisition and control system 800b of FIG. 8B may be used with separated transmitter and receiver antennas, such as the transmitter and receiver antennas 702a,b of FIG. 7B. Those skilled in the art will readily appreciate, however, that the data acquisition and control systems 800a,b described herein are merely examples of a wide variety of data acquisition systems that can operate in accordance with the principles of this disclosure. Accordingly, the data acquisition and control systems 800a,b are not to be limited solely to the specific details described herein and other changes or alterations to the structure and processing capabilities may be introduced without departing from the scope of the disclosure.

As illustrated, the data acquisition and control systems 800a,b may each include at least one transmitter antenna $802_a$-$802_n$. The data acquisition and control system 800b may further include at least one receiver antenna $804_a$-$804_m$, but in the data acquisition and control system 800a, the transmitter antennas $802_{a-n}$ may also operate as receiver antennas. Accordingly, the transmitter antennas $802_{a-n}$ of FIG. 8A may alternatively be characterized as transceivers (i.e., the transceiver antenna 700 of FIG. 7A). Moreover, each transmitter antenna $802_{a-n}$ and each receiver antenna $804_{a-m}$ may comprise or otherwise include any of the azimuthal antenna arrays described herein. Each transmitter antenna $802_{a-n}$ in both data acquisition and control systems $800a,b$ may be driven by a corresponding transmitter $806_a$-$806_n$.

In FIG. 8A, the transmitter antennas $802_{a-n}$ (i.e., transceivers) may each be coupled to a dedicated receiver $808_{a-m}$ or a single receiver 808, and in FIG. 8B, each receiver antenna $804_{a-m}$ may be coupled to a corresponding receiver $808_{a-m}$. It should be noted that the number "m" of receiver antennas $804_{a-m}$ may be the same as, or different from, the number "n" of transmitter antennas $802_{a-n}$. It is also not necessary for the number of receiver antennas $804_{a-m}$ to be the same as the number of receivers $808_{a-m}$, or for the number of transmitter antennas $802_{a-n}$ to be the same as the number of transmitters $806_{a-n}$. Rather, any number of these elements or components may be used or otherwise employed without departing from the scope of the disclosure.

The data acquisition and control systems $800a,b$ may further include transmitter electronics that may include, for example, one or more of a signal generator 810, a digital-to-analog converter 812, a demultiplexer (not shown), and other modules or devices used to support operation of the transmitters $806_{a-n}$. The signal generator 810 may be configured to generate digital signals for transmission by the transmitters $806_{a-n}$, the digital-to-analog converters 812 may be configured to convert the digital signals to analog signals, and the demultiplexer may be configured to selectively couple the signal generator 810 to the transmitters $806_{a-n}$. As will be appreciated, any combination of one or more signal generators 810, digital-to-analog converters 812, and demultiplexers may be used to drive the transmitters $806_{a-n}$. Alternatively, the transmitters $806_{a-n}$ may each perform the function of the signal generator 810, and the signal generator 810 may otherwise be omitted from the data acquisition and control systems $800a,b$.

The receivers $808_{a-m}$ may be coupled to receiver electronics, which may include, for example, one or more analog-to-digital converters 814 and other modules or devices used to support operation of the receivers $808_{a-m}$. A system control center 816 may communicably couple the transmitter and receiver electronics and thereby control overall operation of the data acquisition and control systems $800a,b$. The system control center 816 may further be communicably coupled to at least a data acquisition unit 818 and a data processing and communication unit 820, thereby placing the receiver electronics also in communication with such components. In some embodiments, the data acquisition unit 818 may be configured to determine an amplitude and/or a phase of a received signal. The acquired signal information may be stored, along with acquisition time information in a data buffer of the data acquisition unit 818. The data buffer may be useful when pipe characteristics or features are determined based on signals received at different times and/or at different positions within a wellbore.

Data processing may be performed at the earth's surface or at a downhole location where the data acquisition and control systems $800a,b$ are arranged. If the data processing is to be performed at the surface, the acquired signal information from the receiver electronics, the data acquisition unit 818, and the buffered signal information from the data buffer may be conveyed to the data processing and communication unit 820, which may be configured to transmit the data to the surface 822 and to a computer or other processing system (not shown) arranged at the surface 822. For instance, the data may be transmitted to the logging facility 120 and associated computing facilities 122 of FIG. 1. If the data processing is to be performed downhole, however, the data processing and communication unit 820, in conjunction with the other components of the data acquisition and control systems $800a,b$, may be configured to perform the necessary data processing.

Both the computer at the surface 822 (e.g., the computing facilities 122 of FIG. 1) and the system control center 816 may include multiple processors and a memory configured to receive and store data. The memory may be any non-transitory machine-readable medium that has stored therein at least one computer program with executable instructions that cause the processor(s) to perform the data processing on the received signals. The memory may be, for example, random access memory (RAM), flash memory, read only memory (ROM), programmable read only memory (PROM), electrically erasable programmable read only memory (EEPROM), registers, hard disks, removable disks, a CD-ROM, a DVD, any combination thereof, or any other suitable storage device or medium.

Since the system control center 816 is coupled to various components of the data acquisition and control systems $800a,b$, the system control center 816 may be configured to adjust or otherwise regulate various parameters of the data acquisition and control systems $800a,b$ in order to optimize operation. For example, the system control center 816 may control the frequencies generated by the signal generator 810 in the transmitter electronics or the transmitters $806_{a-n}$. The system control center 816 may also control the timing of the transmitters $806_{a-n}$. For instance, the system control center 816 may cause the transmitters $806_{a-n}$ to operate such that a time-varying signal is generated at the transmitter antennas $802_{a-n}$. The time-varying signal may be sinusoidal with the phase and amplitude of it controlled to a desired value. It may also be a pulse of different shape such as rectangular or triangular.

The digital-to-analog converters 812 may be used to generate electrical signals on the transmitters $806_{a-n}$ that are stored or defined in digital form. The signals that are generated at the transmitters $806_{a-n}$ are coupled electromagnetically to the features or characteristics of the wellbore pipes that are next to the transmitter antennas $802_{a-n}$ and generate eddy currents, which generate secondary currents. These secondary currents contain information about the characteristics of the pipes and they are received by the transmitter antennas $802_{a-n}$ acting as transceivers in FIG. 8A, or by the receiver antennas $804_{a-m}$ of FIG. 8B.

In the case of frequency-domain operation, the received signals can be represented as voltage or current numbers in complex domain with real and imaginary parts, in phasor domain as amplitude and phase, or any other domain that can be obtained by analytical mapping from any of these domains. In the time-domain operation, received signals are magnitudes as a function of time, which can be positive or negative. Results from time and frequency domain can be transferred from one to another by using Fourier transform or inverse Fourier transform. Results may be transferred from analog to digital domain through the use of the analog-to-digital converters 814.

In addition to the eddy currents, which exhibit pipe feature (characteristic) information, a direct coupling from the transmitters $806_{a-n}$ to the receivers $808_{a-m}$ exists. In the case of separated transmitters $806_{a-n}$ and receivers $808_{a-m}$, this coupling term is relatively small, however, it can get relatively big in the case of collocated transmitters $806_{a-n}$ and receivers $808_{a-m}$. This direct coupling can be removed by software through the use of an additive term, which is computed in an air calibration step. An alternative is to remove the coupling by cancelling it out with signals from a secondary transmitter $806_{a-n}$.

In other embodiments, a pulsed excitation may be used with temporally separated transmitting and receiving cycles. In the listening period, the direct coupling dies out polynomially or exponentially and only reflections, scattering, or eddy currents from the features are received. In the sinusoidal type excitation, the length of the listening period determines the signal-to-noise ratio (SNR) of the system. Longer listening times are required to improve SNR, while this also causes slower logging speeds for a fixed vertical resolution for the system.

The sampling frequency also can be optimized to reduce noise while producing enough definition in time to resolve pipe features at different distances to the pipe inspection tool. Listening time is also an important parameter, since features of the pipes that are far away generally arrive at late time. Since downhole memory is limited, it is important to minimize listening time while still maintaining the sensitivity to features that are further away from the pipe inspection tool, such as features (characteristics) of second or third pipes. For a specific transmitter $806_{a-n}$ excitation, multiple receivers $808_{a-m}$ can be recorded at the same time. Similarly, multiple transmitters $806_{a-n}$ can be operated at the same time and they can be time, frequency, or jointly multiplexed for later demultiplexing operations at the receivers $808_{a-m}$. Upon reception of the signals, they are digitized, stored in a buffer, preprocessed, and sent to the surface 822 using the data processing and communication unit 820. The data may later be inverted and the results of the inversion or raw data can be visualized. Decisions on what to do with the pipes being monitored can be made based on the visualization logging or production.

The main difference between the data acquisition and control systems 800a,b (i.e., transceiver and separate transmitter-receiver configurations, respectively) is in the dynamic range of the system and type of electronic design that will be used. A transceiver-type system, for example, requires good control on the transmitting pulse since any ringing in the electronics can impede reception of much smaller received response signals. However, since the same transmitter antenna $802_{a-n}$ (i.e., transceiver) is used for transmitting and receiving in the first data acquisition and control system 800a, significant savings in space can be made, which can translate to space for more windings or higher quality electronics or mechanical parts (such as pressure compensation).

Figure 9:
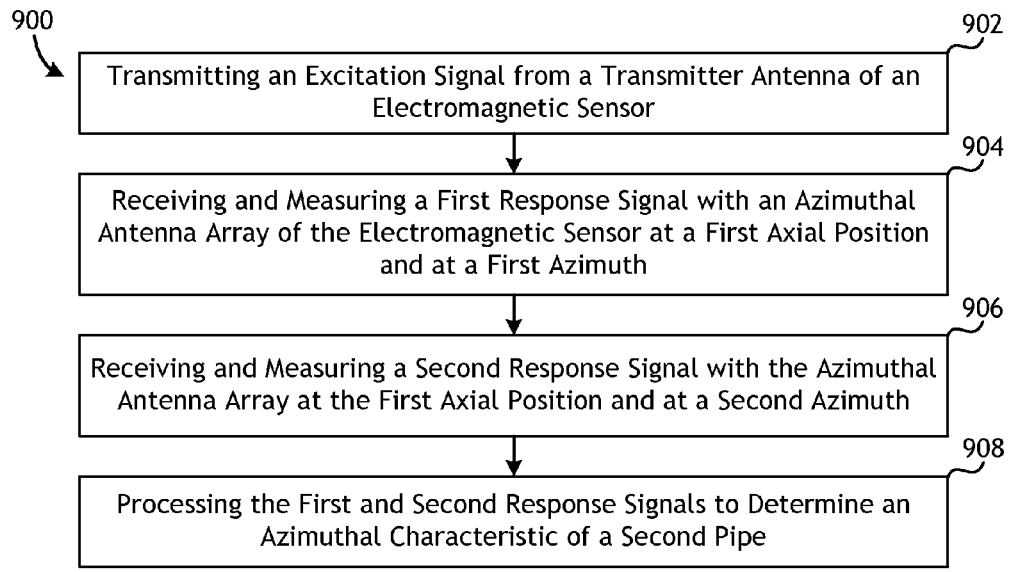
FIG. 9 is a schematic flowchart of a first exemplary interpretation method.

FIG. 9 is a schematic flowchart of a first interpretation method 900, according to one or more embodiments. The method 900 may be undertaken using any of the pipe inspection tools described herein within a wellbore having at least a first pipe and a second pipe (i.e., the first and second pipes 108a,b of FIGS. 2 and 6) positioned therein. According to the method 900, an excitation signal is transmitted from a transmitter antenna of an electromagnetic sensor, as at 902. A first response signal derived from the excitation signal is then received and measured by an azimuthal antenna array of the electromagnetic sensor at a first axial position and at a first azimuth, as at 904. As used in the method 900, and the subsequently described methods, the term "azimuth" refers to a specific or particular angular or circumferential location within the wellbore. The azimuthal antenna array may include a plurality of elongated z-coils or a plurality of separated x-coils and y-coils.

A second response signal may then be received and measured by the azimuthal antenna array at the first axial position and at a second azimuth, as at 906. The first and second response signals can provide distinct information about wellbore pipes beyond the first pipe 108a and they can be used together to calculate a feature or characteristic of the pipes 108a,b through inversion. Accordingly, the first and second response signals may then be compared and otherwise processed to determine an azimuthal characteristic on the second pipe, as at 908. Example azimuthal characteristics that may be determined include, but are not limited to, the presence of a defect (e.g., corrosion, fractures, holes, decreased wall thickness, and changes in magnetic permeability) in the pipes.

In some embodiments, processing the response signals, as at 908, may include comparing the first and second response signals to modeled signals from a computer model. The computer model may be created as a function of various characteristics associated with wellbore pipes beyond the first pipe. A numerical optimization problem may then be solved to minimize a difference between the response signals and the modeled signals by conducting a search in the pipe characteristic space. The pipe characteristic that produces the smallest difference between the modeled signal and response signal may be taken as the solution. With a large enough number of azimuthal antenna array measurements, it may be possible to calculate a high-resolution image of the wellbore pipes beyond the first pipe.

Figure 10:
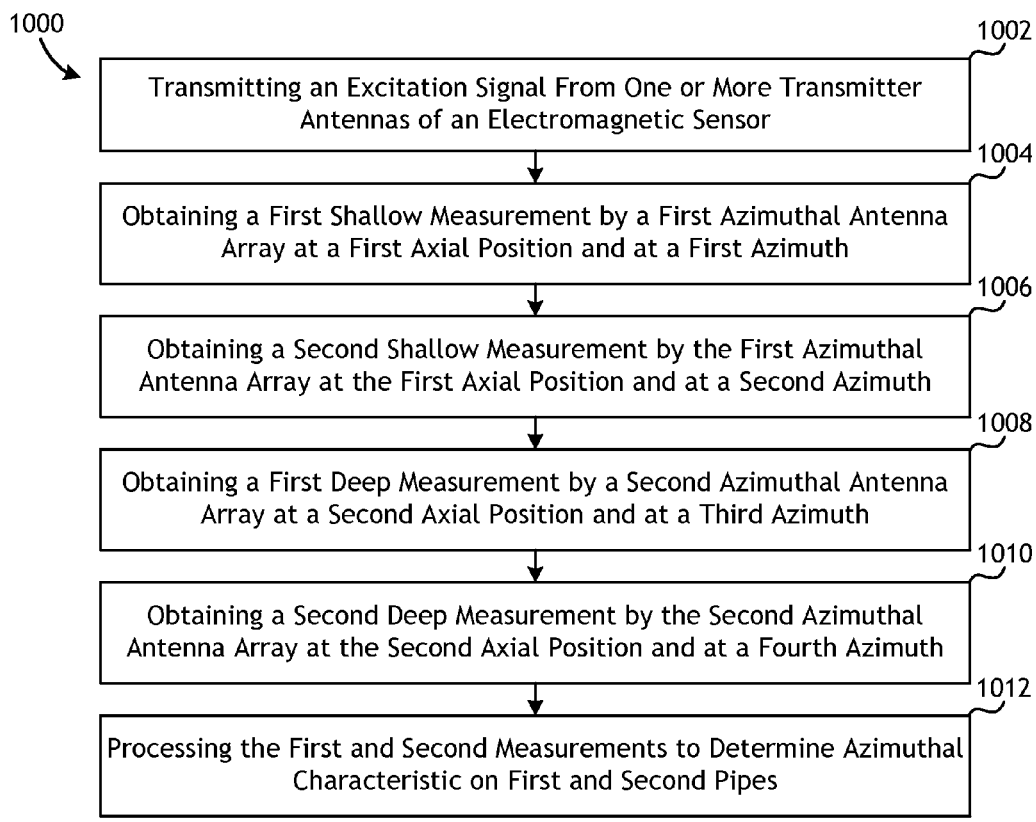
FIG. 10 is a schematic flowchart of a second exemplary interpretation method.

FIG. 10 is a schematic flowchart of a second interpretation method 1000, according to one or more embodiments. Similar to the method 900 of FIG. 9, the method 1000 may be undertaken using any of the pipe inspection tools described herein within a wellbore having at least a first pipe and a second pipe (i.e., the first and second pipes 108a,b of FIGS. 2 and 3) positioned therein. According to the method 1000, an excitation signal is transmitted from a transmitter antenna of an electromagnetic sensor, as at 1002. A first shallow measurement derived from the excitation signal is then received and measured by a first azimuthal antenna array of the electromagnetic sensor at a first axial position and at a first azimuth, as at 1004. Here, shallow measurement is one that is made with a smaller transmitter-to-receiver distance (for non-collocated transmitter-receivers) or smaller length (for collocated transmitter-receivers), compared to a deep measurement configuration. For example, in case the same receiver array is used for shallow and deep measurements, a transmitter that is farther away may be used to make the deep measurement as compared to a transmitter used for the shallow measurement. The first azimuthal antenna array may include a first plurality of elongated z-coils or a first plurality of separated x-coils and y-coils. In at least one embodiment, the pipe inspection tool may be eccentrically located within the first pipe 108a. A second shallow measurement derived from the excitation signal is then received and measured by the first azimuthal antenna array at the first axial position and at a second azimuth, as at 1006.

A first deep measurement derived from the excitation signal is then received and measured by a second azimuthal antenna array of the electromagnetic sensor at the first axial position and at a third azimuth, as at 1008. In some embodiments, the second azimuthal antenna array may include a second plurality of elongated z-coils or a second plurality of separated x-coils and y-coils. In other embodiments, however, the second azimuthal array may be the same as the first azimuthal array, without departing from the scope of the disclosure. A second deep measurement derived from the excitation signal is then received and measured by the second azimuthal antenna array at the second axial position and at a fourth azimuth, as at 1010. In at least one embodiment, the first and second azimuths where the first and second shallow measurements are obtained, as at 1004 and 1006, may be the same as the third and fourth azimuths where the first and second deep measurements are obtained, as at 1008 and 1010. Moreover, in at least one embodiment, the first axial position where the first and second shallow measurements are obtained, as at 1004 and 1006, may be the same as the second axial position where the third and fourth deep measurements are obtained, as at 1008 and 1010. In such an embodiment, transmitters at different distances from the receiver axial position may be used to obtain the shallow and deep measurements. Finally, the first and second shallow measurements and the first and second deep measurements may be processed to determine azimuthal characteristics on the first and second pipes, as at 1012.

Figure 11:
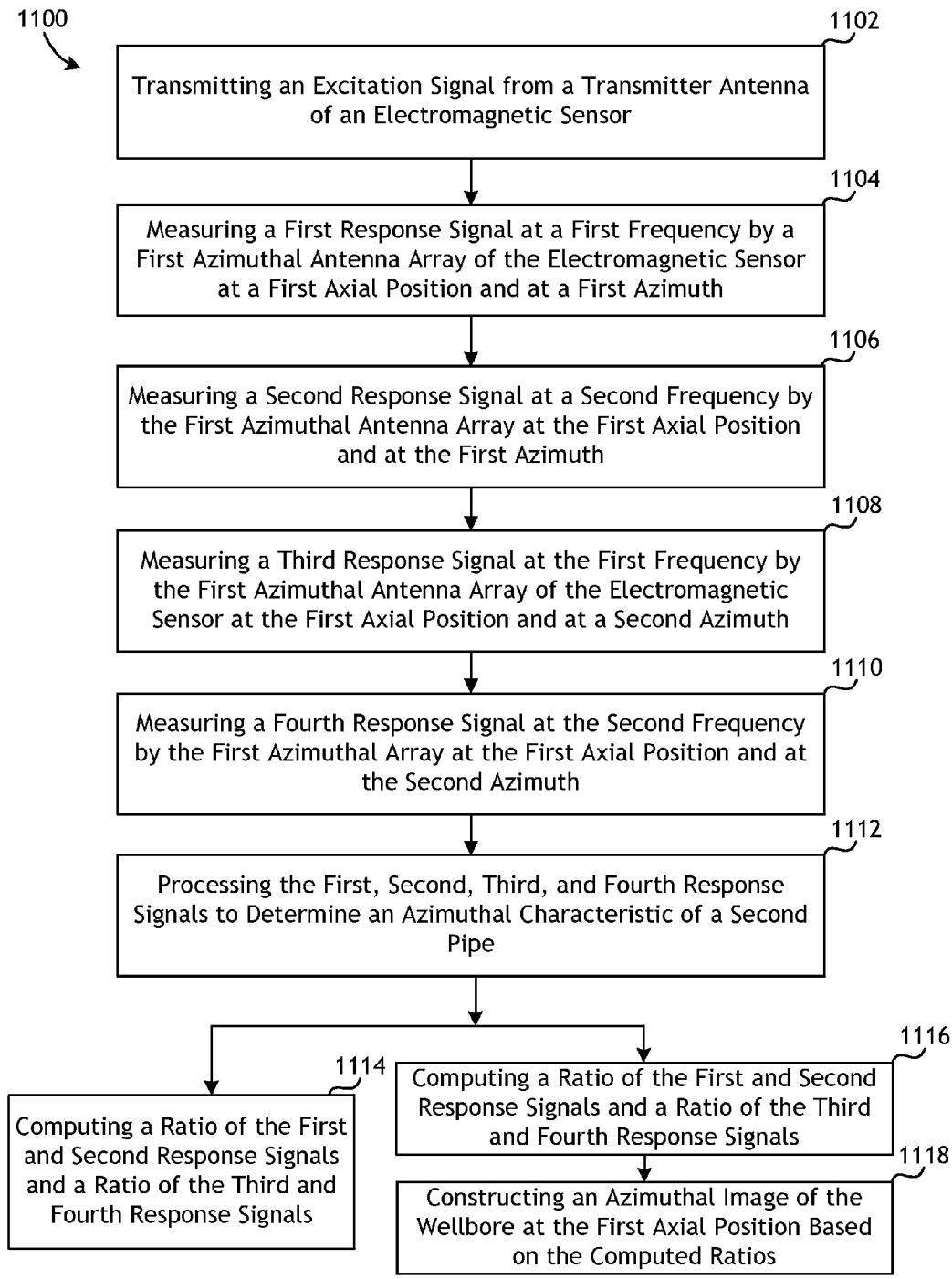
FIG. 11 is a schematic flowchart of a third exemplary interpretation method.

FIG. 11 is a schematic flowchart of a third interpretation method 1100, according to one or more embodiments. Similar to the methods 900, 1000 of FIGS. 9 and 10, respectively, the method 1100 may be undertaken using any of the pipe inspection tools described herein within a wellbore having at least a first pipe and a second pipe (i.e., the first and second pipes 108a,b of FIGS. 2 and 3) positioned therein. According to the method 1100, an excitation signal is transmitted from a transmitter antenna of an electromagnetic sensor, as at 1102. A first response signal derived from the excitation signal is then received and measured at a first frequency by a first azimuthal antenna array of the electromagnetic sensor at a first axial position and at a first azimuth, as at 1104. The first azimuthal antenna array may include a first plurality of elongated z-coils or a first plurality of separated x-coils and y-coils. In at least one embodiment, the pipe inspection tool may be eccentrically located within the first pipe 108a.

A second response signal derived from the excitation signal may then be received and measured at a second frequency by the first azimuthal antenna array at the first axial position and at the first azimuth, as at 1106, where the second frequency is greater than the first frequency. A third response signal derived from the excitation signal may then be received and measured at the first frequency by the first azimuthal antenna array at the first axial position and at a second azimuth, as at 1108. A fourth response signal derived from the excitation signal may then be received and measured at the second frequency by the first azimuthal antenna array at the first axial position and at the second azimuth, as at 1110.

The first, second, third, and fourth response signals may then be processed to determine an azimuthal characteristic on the second pipe 108b or otherwise on any pipes beyond the first pipe 108a, as at 1112. In some embodiments, this may be accomplished by computing a ratio of the first and second response signals and computing a ratio of the third and fourth response signals, as at 1114. In other embodiments, this may alternatively be accomplished by computing the ratios of the first and second responses and the third and fourth responses, as at 1116, and subsequently constructing an azimuthal image of the wellbore at the first axial position based on the ratios, as at 1118. Accordingly, in such a scenario, multiple ratios from around the wellbore may be plotted as a function of antenna azimuth and depth, and subsequently recorded and shown as an image.

Figure 12:
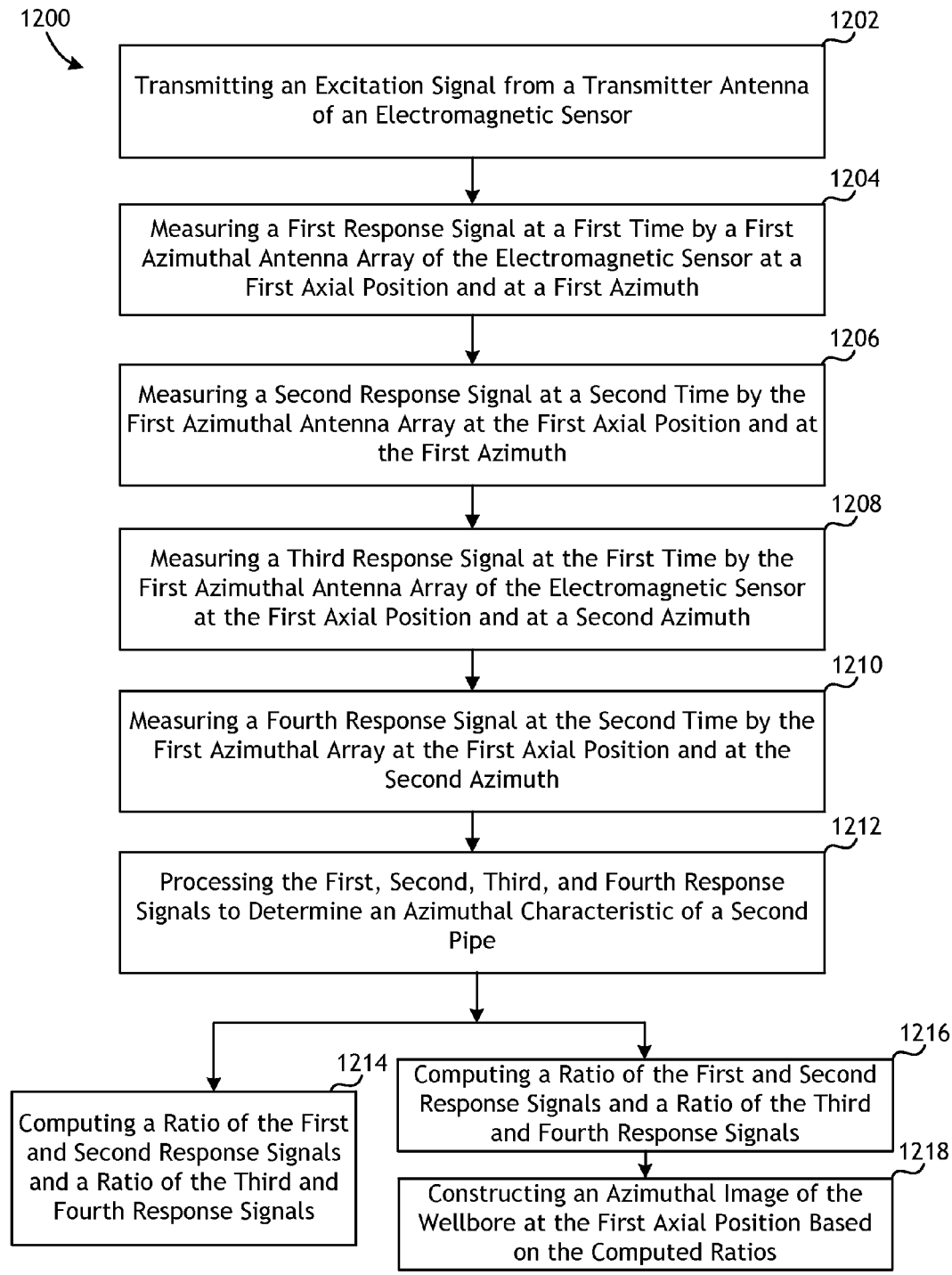
FIG. 12 is a schematic flowchart of a fourth exemplary interpretation method.

FIG. 12 is a schematic flowchart of a fourth interpretation method 1100, according to one or more embodiments. Similar to the methods 900, 1000, and 1100 of FIGS. 9, 10, and 11, respectively, the method 1200 may be undertaken using any of the pipe inspection tools described herein within a wellbore having at least a first pipe and a second pipe (i.e., the first and second pipes 108a,b of FIGS. 2 and 3) positioned therein. Moreover, the method 1200 may be similar to the third method 1100, except that time data may be used in the place of frequency data. According to the method 1200, an excitation signal is transmitted from a transmitter antenna of an electromagnetic sensor, as at 1202. A first response signal derived from the excitation signal is then received and measured at a first time by a first azimuthal antenna array of the electromagnetic sensor at a first axial position and at a first azimuth, as at 1204. The first azimuthal antenna array may include a first plurality of elongated z-coils or a first plurality of separated x-coils and y-coils. In at least one embodiment, the pipe inspection tool may be eccentrically located within the first pipe 108a.

A second response signal derived from the excitation signal may then be received and measured at a second time by the first azimuthal antenna array at the first axial position and at the first azimuth, as at 1206, where the second time is greater or longer than the first time. A third response signal derived from the excitation signal may then be received and measured at the first time by the first azimuthal antenna array at the first axial position and at a second azimuth, as at 1208. A fourth response signal derived from the excitation signal may then be received and measured at the second time by the first azimuthal antenna array at the first axial position and at the second azimuth, as at 1210.

The first, second, third, and fourth response signals may then be processed to determine an azimuthal characteristic on the second pipe 108b or otherwise on any pipes beyond the first pipe 108a, as at 1212. In some embodiments, this may be accomplished by computing a ratio of the first and second response signals and computing a ratio of the third and fourth response signals, as at 1214. In other embodiments, this may alternatively be accomplished by computing the ratios of the first and second responses and the third and fourth responses, as at 1216, and subsequently constructing an azimuthal image of the wellbore at the first axial position based on the ratios, as at 1218. Accordingly, in such a scenario, multiple ratios from around the wellbore may be plotted as a function of antenna azimuth and depth, and subsequently recorded and shown as an image.

Figure 13:
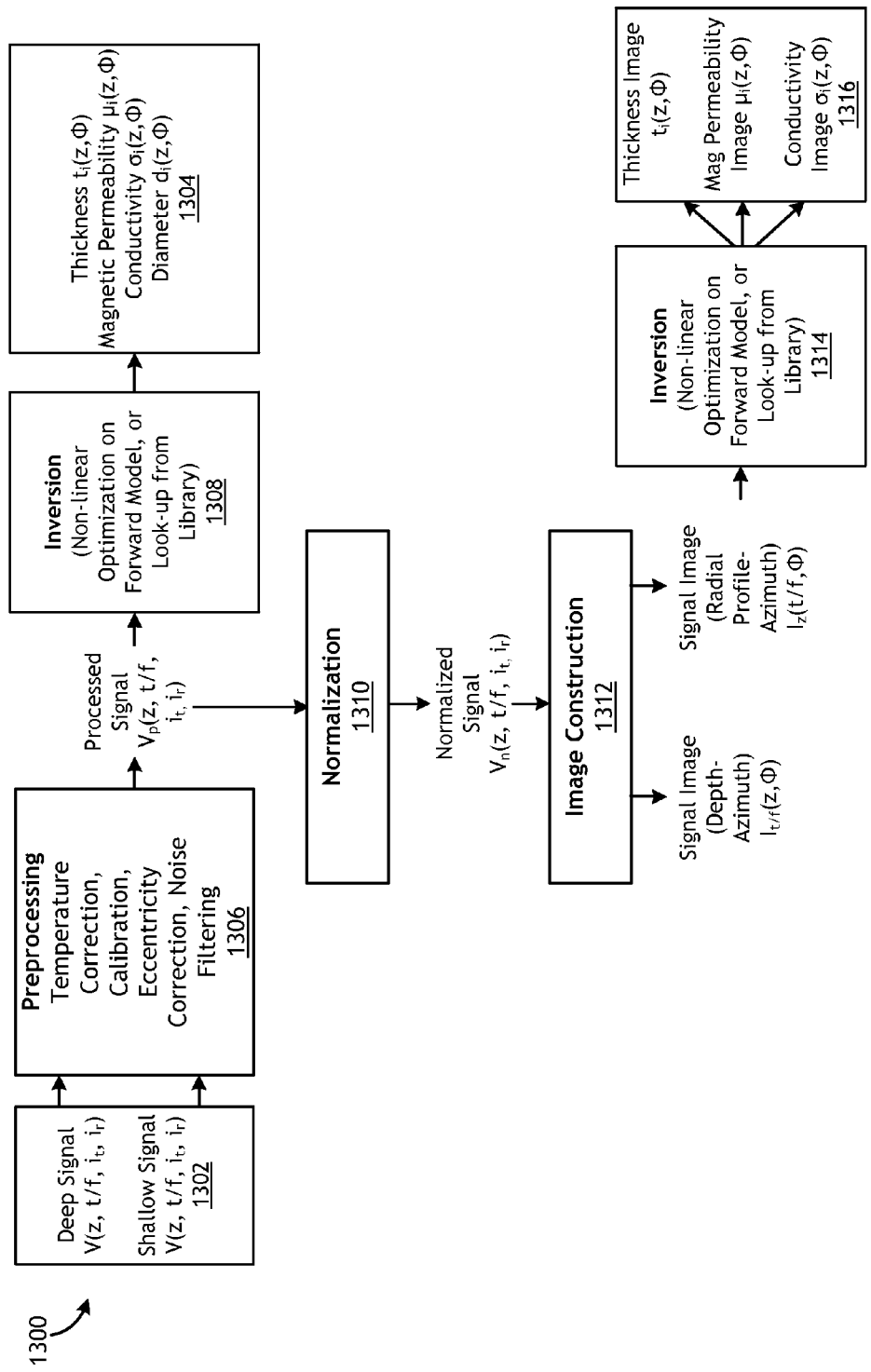
FIG. 13 is a schematic flowchart depicting the presently described inversion methodology.

FIG. 13 is a schematic flowchart of a method 1500 that shows a more detailed description of the presently described inversion methodology. More particularly, the method 1500 may take measurement data 1302 in the form of deep and shallow impedance signals V at depth z and convert them into one or more pipe characteristics 1304 such as, but not limited to, thickness, magnetic permeability, conductivity, and diameter measurements of any of the pipes (i.e., the pipes 108a,b of FIGS. 2 and 6).

In the illustrated method, deep and shallow signals V are measured at time t (for frequency and time-based systems) at antenna depth z between the antenna terminals $i_{r1}$ and $i_{r2}$ as a result of excitation between the antenna terminals $i_{t1}$ and $i_{t2}$. The received signals V and, more particularly, the transmitter index $i_t$ and the receiver index $i_r$, may then be preprocessed, as at 1306. Preprocessing the measurement data 1302 may include performing temperature corrections through the use of correlation tables or performing "software focusing" to remove drifts in the electronics. Preprocessing the measurement data 1302 may also include calibration, which may include normalization with the excitation signal amplitude, eccentricity (standoff) correction, to remove the effect of a sensor pad 506 (FIGS. 5D-5F), if used, not touching the pipe, and temporal or spatial filters to reduce noise.

The preprocessed signal Vp may then be fed to an inversion algorithm, as at 1308, which looks up the measured signal in a database that contains mappings between modeled signals and pipe features (thickness, magnetic permeability, conductivity and diameter). The pipe characteristics corresponding to the modeled signal that matches with least mismatch with the measured processed signal may then be selected. When applied at different depths, the inversion algorithm may yield various pipe characteristics 1304, such as thickness, magnetic permeability, conductivity and diameter of the pipe as a function of depth and azimuth in the wellbore.

The preprocessed signal Vp may optionally be normalized, as at 1310, and images may be constructed of the normalized signals Vn, as at 1312. A similar inversion method may then be applied on the normalized signal images at a different depth, azimuth, time or frequency, as at 1314. The resulting signals may be plotted as a function of depth and azimuth, which yields traditional logging pipe images. For instance, signals may be plotted as a function of depth and azimuth, which yields traditional logging pipe images. Signals may also be plotted as a function of time/frequency and azimuth, which yields a cross-section view of the hole since different frequency and time is influenced by different pipes. Finally, thickness, magnetic permeability and conductivity from the inversion results may be plotted as a function of depth z and azimuth, as at 1316.

According to the schematic diagram of FIG. 13, first shallow and deep signals that are received at depth z, at frequency for time t (for frequency and time-based systems), transmitter index $i_t$ and receiver index $i_r$ is preprocessed. The preprocessing step may be composed of temperature correction, calibration, eccentricity correction, and noise filtering, and may yield processed signals. Next, inversion may be performed on the processed signals, which is a numerical optimization that finds the pipe features that optimally match the modeled signals to those from the measurements based on a pipe parameterization. When applied at a different depth, it may yield thickness, magnetic permeability, conductivity and diameter of the pipe as a function of depth and azimuth in the borehole.

Embodiments disclosed herein include:

A. A pipe inspection tool that includes a body having a central axis, and one or more azimuthal antenna arrays operatively coupled to the body, each azimuthal antenna array including a plurality of antenna coils arranged circumferentially about the central axis and comprising at least one of an azimuthal array of z-coils, an azimuthal array of separated x-coils, and an azimuthal array of separated y-coils, wherein the separated x-coils are oriented in a first direction with respect to the central axis, the separated y-coils are oriented in a second direction with respect to the central axis, and the z-coils are oriented in a third direction with respect to the central axis, and wherein the second direction is orthogonal to the first direction, and the third direction is orthogonal to both the first and second directions.

B. A method that includes conveying a pipe inspection tool into a wellbore having at least a first pipe positioned within a second pipe, the pipe inspection tool including one or more azimuthal antenna arrays, where each azimuthal antenna array includes at least one of an azimuthal array of z-coils, an azimuthal array of separated x-coils, and an azimuthal array of separated y-coils, transmitting an excitation signal from a transmitter antenna of the pipe inspection tool, measuring a first response signal derived from the excitation signal with one of the one or more azimuthal antenna arrays at an axial position within the wellbore and at a first azimuth, measuring a second response signal with the one of the one or more azimuthal antenna arrays at the axial position and at a second azimuth, and processing the first and second response signals to determine an azimuthal characteristic of the second pipe.

C. A method that includes conveying a pipe inspection tool into a wellbore having at least a first pipe positioned within a second pipe, the pipe inspection tool including one or more azimuthal antenna arrays, where each azimuthal antenna array includes at least one of an azimuthal array of z-coils, an azimuthal array of separated x-coils, and an azimuthal array of separated y-coils, transmitting an excitation signal from a transmitter antenna of the pipe inspection tool, measuring a first shallow measurement derived from the excitation signal with a first azimuthal antenna array at a first axial position within the wellbore and at a first azimuth, measuring a second shallow measurement derived from the excitation signal with the first azimuthal antenna array at the first axial position and at a second azimuth, measuring a first deep measurement derived from the excitation signal with a second azimuthal antenna array at the second axial position and at a third azimuth, measuring a second deep measurement derived from the excitation signal with the second azimuthal antenna array at the second axial position and at a fourth azimuth, and processing the first and second shallow measurements and the first and second deep measurements to determine azimuthal characteristics of the first and second pipes.

Each of embodiments A, B, and C may have one or more of the following additional elements in any combination: Element 1: wherein the one or more azimuthal antenna arrays are axially spaced from each other along a length of the body. Element 2: wherein at least one of the one or more azimuthal antenna arrays is mounted on a plurality of deployable sensor pads. Element 3: wherein the separated x-coils are aligned along a common plane that extends in the first direction, and the separated y-coils are aligned along a common plane that extends in the second direction. Element 4: wherein the separated x-coils are aligned along parallel planes that extend in the first direction, and the separated y-coils are aligned along parallel planes that extend in the second direction. Element 5: wherein some or all of the z-coils are elongated z-coils.

Element 6: wherein the separated x-coils or the separated y-coils are at least twice larger in an axial direction as compared to an azimuthal direction. Element 7: wherein processing the first and second response signals comprises comparing the first and second response signals to modeled signals from a computer model, solving a numerical optimization problem to minimize a difference between the first and second response signals and the modeled signals, wherein the numerical optimization problem is solved by conducting a search of stored pipe characteristics, and determining the azimuthal characteristic of the second pipe based on the stored pipe characteristic that produces a smallest difference between the modeled signal and the first and second response signals. Element 8: wherein the first response signal is measured at a first frequency or at a first time, and the second response signal is measured at a second frequency or a second time, the method further comprising measuring a third response signal derived from the excitation signal at the first frequency or the first time with the first azimuthal antenna array at the first axial position and at a second azimuth, measuring a fourth response signal derived from the excitation signal at the second frequency or the second time with the first azimuthal antenna array at the first axial position and at the second azimuth, and processing the first, second, third, and fourth response signals to determine the azimuthal characteristic of the second pipe. Element 9: wherein processing the first, second, third, and fourth response signals comprises computing a ratio of the first and second response signals, computing a ratio of the third and fourth response signals, and comparing the ratios of the first and second and the third and fourth response signals to solve for the azimuthal characteristic of the second pipe. Element 10: wherein processing the first, second, third, and fourth response signals comprises computing a ratio of the first and second response signals, computing a ratio of the third and fourth response signals, and constructing an azimuthal image of the wellbore at the first axial position based on the ratios. Element 11: further comprising generating a two-dimensional (2D) image of the second pipe based on the azimuthal characteristic of the second pipe. Element 12: wherein a first dimension of the 2D image is derived from azimuth angle and a second dimension of the 2D image is derived from one of depth within the wellbore, frequency, and time.

Element 13: further comprising generating images of the first and second pipes based on the azimuthal characteristics of the first and second pipes. Element 14: further comprising generating a two-dimensional (2D) image of the second pipe based on the azimuthal characteristics of the first and second pipes. Element 15: wherein a first dimension of the 2D image is derived from azimuth angle and a second dimension of the 2D image is derived from one of depth within the wellbore, frequency, and time. Element 16: wherein the separated x-coils or the separated y-coils are at least twice larger in the axial direction as compared to an azimuthal direction.

By way of non-limiting example, exemplary combinations applicable to A, B, and C include: Element 7 with Element 8; Element 8 with Element 9; Element 8 with Element 10; Element 10 with Element 11; Element 8 with Element 11; Element 11 with Element 12; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A pipe inspection tool, comprising:
    a body having a central axis; and
    a plurality of azimuthal antenna arrays operatively coupled to the body, each azimuthal antenna array including a plurality of antenna coils arranged circumferentially about the central axis, the plurality of azimuthal antenna arrays comprising an azimuthal array of z-coils, an azimuthal array of separated x-coils, and an azimuthal array of separated y-coils,
    wherein the plurality of antenna coils of the azimuthal array of separated x-coils are oriented in a first direction with respect to the central axis, the plurality of antenna coils of the azimuthal array of separated y-coils are oriented in a second direction with respect to the central axis, and the plurality of antenna coils of the azimuthal array of z-coils are oriented in a third direction with respect to the central axis, and wherein the second direction is orthogonal to the first direction, and the third direction is orthogonal to both the first and second directions.

2. The pipe inspection tool of claim 1, wherein at least two of the azimuthal antenna arrays are axially spaced from each other along a length of the body.

3. The pipe inspection tool of claim 1, wherein at least one of the azimuthal antenna arrays is mounted on a plurality of deployable sensor pads.

4. The pipe inspection tool of claim 1, wherein the antenna coils of the azimuthal array of separated x-coils are aligned along a common plane that extends in the first direction, and the antenna coils of the azimuthal array of separated y-coils are aligned along a common plane that extends in the second direction.

5. The pipe inspection tool of claim 1, wherein at least two of the antenna coils of the azimuthal array of separated x-coils are aligned along parallel planes that extend in the first direction, and at least two of the antenna coils of the azimuthal array of separated y-coils are aligned along parallel planes that extend in the second direction.

6. The pipe inspection tool of claim 1, wherein some or all of the z-coils are elongated z-coils.

7. A method, comprising:
    conveying a pipe inspection tool into a wellbore having at least a first pipe positioned within a second pipe, the pipe inspection tool including a plurality of azimuthal antenna arrays including an azimuthal array of separated x-coils and an azimuthal array of separated y-coils;

transmitting an excitation signal from a transmitter antenna of the pipe inspection tool;

measuring a first response signal derived from the excitation signal with one of the azimuthal antenna arrays at an axial position within the wellbore and at a first azimuth;

measuring a second response signal with the one of the azimuthal antenna arrays at the axial position and at a second azimuth; and processing the first and second response signals to determine an azimuthal characteristic of the second pipe.

8. The method of claim 7, wherein the azimuthal array of separated x-coils or the azimuthal array of separated y-coils includes at least one antenna coil that is at least twice larger in an axial direction as compared to an azimuthal direction.

9. The method of claim 7, wherein processing the first and second response signals comprises:

comparing the first and second response signals to modeled signals from a computer model;

solving a numerical optimization problem to minimize a difference between the first and second response signals and the modeled signals, wherein the numerical optimization problem is solved by conducting a search of stored pipe characteristics; and determining the azimuthal characteristic of the second pipe based on the stored pipe characteristic that produces a smallest difference between the modeled signal and the first and second response signals.

10. The method of claim 9, further comprising generating a two-dimensional (2D) image of the second pipe based on the azimuthal characteristic of the second pipe.

11. The method of claim 7, wherein the first response signal is measured at a first frequency or at a first time, and the second response signal is measured at a second frequency or a second time, the method further comprising:

measuring a third response signal derived from the excitation signal at the first frequency or the first time with the one of the azimuthal antenna arrays at the axial position and at the second azimuth;

measuring a fourth response signal derived from the excitation signal at the second frequency or the second time with the one of the azimuthal antenna arrays at the axial position and at the second azimuth; and processing the first, second, third, and fourth response signals to determine the azimuthal characteristic of the second pipe.

12. The method of claim 11, wherein processing the first, second, third, and fourth response signals comprises:

computing a ratio of the first and second response signals;

computing a ratio of the third and fourth response signals; and comparing the ratios of the first and second and the third and fourth response signals to solve for the azimuthal characteristic of the second pipe.

13. The method of claim 11, wherein processing the first, second, third, and fourth response signals comprises:

computing a ratio of the first and second response signals;

computing a ratio of the third and fourth response signals; and constructing an azimuthal image of the wellbore at the axial position based on the ratios.

14. The method of claim 13, further comprising generating a two-dimensional (2D) image of the second pipe based on the azimuthal characteristic of the second pipe.

15. The method of claim 14, wherein a first dimension of the 2D image is derived from azimuth angle and a second dimension of the 2D image is derived from one of depth within the wellbore, frequency, and time.

16. A method, comprising:

conveying a pipe inspection tool into a wellbore having at least a first pipe positioned within a second pipe, the pipe inspection tool including a plurality of azimuthal antenna arrays including an azimuthal array of separated x-coils and an azimuthal array of separated y-coils;

transmitting an excitation signal from a transmitter antenna of the pipe inspection tool;

measuring a first shallow measurement derived from the excitation signal with a first azimuthal antenna array at a first axial position within the wellbore and at a first azimuth;

measuring a second shallow measurement derived from the excitation signal with the first azimuthal antenna array at the first axial position and at a second azimuth;

measuring a first deep measurement derived from the excitation signal with a second azimuthal antenna array at a second axial position and at a third azimuth;

measuring a second deep measurement derived from the excitation signal with the second azimuthal antenna array at the second axial position and at a fourth azimuth; and processing the first and second shallow measurements and the first and second deep measurements to determine azimuthal characteristics of the first and second pipes.

17. The method of claim 16, further comprising generating images of the first and second pipes based on the azimuthal characteristics of the first and second pipes.

18. The method of claim 16, further comprising generating a two-dimensional (2D) image of the second pipe based on the azimuthal characteristics of the first and second pipes.

19. The method of claim 18, wherein a first dimension of the 2D image is derived from azimuth angle and a second dimension of the 2D image is derived from one of depth within the wellbore, frequency, and time.

20. The method of claim 16, wherein the azimuthal array of separated x-coils or the azimuthal array of separated y-coils includes at least one antenna coil that is at least twice larger in an axial direction as compared to an azimuthal direction.

* * * * *